(12) United States Patent
Vukicevic et al.

(10) Patent No.: US 8,119,591 B2
(45) Date of Patent: Feb. 21, 2012

(54) METHODS AND COMPOSITIONS FOR REGENERATING ARTICULAR CARTILAGE

(75) Inventors: Slobodan Vukicevic, Zagreb (HR); Mislav Jelic, Zagreb (HR)

(73) Assignee: Genera Istrazivanja d.o.o., Kalinovica (HR)

( * ) Notice: Subject to any disclaimer, the term of this patent is extended or adjusted under 35 U.S.C. 154(b) by 936 days.

(21) Appl. No.: 11/989,802

(22) PCT Filed: Aug. 1, 2006

(86) PCT No.: PCT/US2006/030077
§ 371 (c)(1),
(2), (4) Date: Jan. 31, 2008

(87) PCT Pub. No.: WO2007/016620
PCT Pub. Date: Feb. 8, 2007

(65) Prior Publication Data
US 2009/0143286 A1 Jun. 4, 2009

Related U.S. Application Data

(60) Provisional application No. 60/704,862, filed on Aug. 1, 2005.

(51) Int. Cl.
*A61K 38/18* (2006.01)
(52) U.S. Cl. .................. 514/1.1; 514/6.9; 514/9.1
(58) Field of Classification Search .................. None
See application file for complete search history.

(56) References Cited

U.S. PATENT DOCUMENTS

| | | | |
|---|---|---|---|
| 4,968,590 | A | 11/1990 | Kuberasampath et al. |
| 5,011,691 | A | 4/1991 | Oppermann et al. |
| 5,376,636 | A | 12/1994 | Rutherford et al. |
| 5,496,552 | A | 3/1996 | Kuberasampath et al. |
| 5,674,844 | A | 10/1997 | Kuberasampath et al. |
| 5,843,899 | A | 12/1998 | Halloran |
| 5,965,573 | A | 10/1999 | Petrie et al. |
| 6,333,312 | B1 | 12/2001 | Kuberasampath et al. |
| 6,511,958 | B1 * | 1/2003 | Atkinson et al. ............ 424/94.4 |
| 2003/0235589 | A1 | 12/2003 | Demopulos et al. |

FOREIGN PATENT DOCUMENTS

| | | |
|---|---|---|
| EP | 0 434 625 A2 | 6/1991 |
| WO | WO 96/39170 A1 | 12/1996 |

OTHER PUBLICATIONS

Asahina et al., *Exp. Cell. Res.*, 222: 38-47 (1996).
Griffith et al., *Proc. Natl. Acad. Sci.* USA, 93: 878-883 (1996).
Jelic et al., *Growth Factors*, 19(2): 101-113 (2001).
Jones et al., *Growth Factors*, 11: 214-225 (1994).
Lories et al., *Ann. Rheum. Dis.*, 62(6): 568-571 (2003).
Luyten et al., *J. Biol. Chem.*, 267(6): 3691-3695 (1992).
Reddi, *J. Bone Joint Surg. Am.*, 83-A (Supp. 1): S1-S6 (2001).
Sampath et al., *Proc. Natl. Acad. Sci* USA, 78: 7599-7603 (1981).
Sampath et al., *Proc. Natl. Acad. Sci.* USA, 84: 7109-7113 (1987).
Urist et al., *Proc. Soc. Exp. Biol. Med.*, 173: 194-199 (1983).
Urist et al., *Proc. Natl. Acad. Sci.* USA, 81: 371-375 (1984).
Vandenabeele et al., *Arch. Histol. Cytol.*, 66(2): 145-153 (2003).
Wang et al., *Proc. Natl. Acad. Sci.* USA, 87: 2220-2224 (1990).
Wozney et al., *Science*, 242: 1528-1534 (1988).
Written Opinion of the International Searching Authority for international application No. PCT/US06/30077 (Jun. 17, 2008).
International Search Report for international application No. PCT/US06/30077 (Jun. 17, 2008).
Boden et al., "Differential effects and glucocorticoid potentiation of bone morphogenetic protein action during rat osteoblast differentiation in vitro," Endocrinology, 137: 3401-3407 (1996).
Itagane et al., "Interactions between steroid hormones and insulin-like growth factor-I in rabbit chondrocytes," Endocrinology, 128: 1419-1424 (1991).
Jones et al., "Pituitary fibroblast growth factor as a stimulator of growth in cultured rabbit articular chondrocytes," Endocrinology, 97: 359-365 (1975).
Pecina et al., "Articular cartilage repair: the role of bone morphogenetic proteins," Int. Orthop., 26: 131-136 (2002).
Robinson et al., "Articular cartilage chondrocytes are more advantageous for generating hyaline-like cartilage than mesenchymal cells isolated from microfracture repairs," Cell Tissue Banking, 2: 23-30 (2001).
Extended European Search Report dated Dec. 20, 2010, issued in corresponding European application No. 06789183.8.
Chang et al., "Cartilage-derived morphogenetic proteins; new members of the transforming growth factor-β superfamily predominantly expressed in long bones during human embryonic development," J. Biol. Chem., 269: 28227-28234 (1994).
Erlacher et al., "Cartilage-derived morphogenetic proteins and osteogenic protein 1 differentially regulate osteogenesis," J. Bone Miner. Res., 13: 383-392 (1998).
Rueger, D.C., "Biochemistry of bone morphogenetic proteins," Chapter 1, In Bone Morphogenetic Proteins, From Laboratory to Clinical Practice, (Vukicevic and Sampath, eds.) (Birkhäuser Verlag, Basel, 2002) pp. 1-18.
Zoricic et al., "Expression of bone morphogenetic proteins and cartilage-derived morphogenetic proteins during osteophyte formation in humans," J. Anat., 202: 269-277 (2003).

\* cited by examiner

*Primary Examiner* — Christopher R. Tate
*Assistant Examiner* — Roy Teller
(74) *Attorney, Agent, or Firm* — Thomas R. Berka; Leon R. Yankwich; Yankwich & Associates, P.C.

(57) ABSTRACT

Methods and compositions are described to regenerate cartilage in a partial thickness defect or area of reduced volume of articular cartilage comprising an infiltration suppressor agent and a columnar growth promoting agent.

17 Claims, 1 Drawing Sheet

METHODS AND COMPOSITIONS FOR REGENERATING ARTICULAR CARTILAGE

CROSS-REFERENCE TO RELATED APPLICATIONS

This application is a United States national stage filing under 35 U.S.C. §371 of international application No. PCT/US2006/030077, filed Aug. 1, 2006, designating the U.S., which claims priority to U.S. Provisional Application No. 60/704,862, filed Aug. 1, 2005.

BACKGROUND OF THE INVENTION

The healthy cartilage of joints (articular cartilage) in humans and other vertebrates is characterized by a columnar growth pattern of chondrocytes, which produce a hyaline cartilage containing predominantly proteoglycans, type II collagen, and water. Articular cartilage provides an effective weight-bearing cushion to prevent bone-to-bone contact of opposing bones in a joint and, thus, is critical to the normal function of the joint. The regeneration of authentic articular cartilage remains a major challenge in modern medicine because the factors initiating cartilage formation, maturation, and healing are poorly understood. Approximately one-half of the knee joints of patients that are examined arthroscopically contain asymptomatic cartilage defects, i.e., most defects in the cartilage do not penetrate completely to the subchondral bone. These "partial thickness defects" in articular cartilage usually are not painful. However, the remaining cartilage at the base of a partial thickness defect may continue to erode and the diameter of the defect may also increase such that the defect eventually progresses to a "full thickness defect" that penetrates to the underlying bone. Such full thickness defects may become large enough that the opposing bones of the joint eventually contact and begin eroding one another leading to inflammation, pain, and degenerative changes, i.e., the classic symptoms of osteoarthritis. Osteoarthritis is a crippling disease that results in joint deformity and that typically affects a patient's quality of life as the patient avoids the pain and instability of using the deformed joint in work and daily living.

Studies of the restoration and healing of joint defects have employed drilling holes in the articular cartilage of animal knee joints. Such defects undergo a form of repair with the formation of a new layer of bone and repair tissue, but the macromolecular organization and the biochemical characteristics of the repair tissue are clearly imperfect as evidenced by the persistence of high levels of type I collagen and the substitution of the cartilage specific proteoglycans with other types, such as dermatan sulfate-containing proteoglycans. The resulting repair tissue is an inferior fibrocartilaginous tissue that exhibits fibrillations and extensive degenerative changes after about three months and that eventually degenerates into a complete loss of tissue integrity and more damage to the joint. Such fibrous repair tissue typically forms at defect sites in all forms of current treatments (see, below). Accordingly, true regeneration of articular cartilage at a defect site in humans and other vertebrates would restore a columnar organization of metabolically active chondrocytes, which produce type II collagen that in combination with certain proteoglycans becomes fully integrated with the cartilage surrounding the defect and thereby restores the full weight bearing capacity of the joint cartilage.

Several procedures are currently in use to treat defects of articular cartilage. A widely used method that seeks to provide repair of a defect site involves debridement of cartilage at the defect site to expose subchondral bone followed by drilling and microfracture (using specialized instruments) to produce tunnels through the subchondral bone to connect the defect site with the bone marrow. Bone marrow cells, which have an aggressive proliferation capacity, then migrate through the tunnels and form fibrocartilage in the defect area. This type of procedure may be performed arthroscopically, which reduces injury to the joint and does not leave a skin scar, may be performed as a one-stage procedure, and is relatively inexpensive. However, the newly formed tissue formed by this procedure has no cartilage architecture, but is entirely made of a fibrocartilage that has a short surviving and low weight bearing capacity. Maximum improvement of symptoms following this procedure may last for two to five years followed by an unsatisfactory longer-term outcome.

Regenerative approaches to restore articular cartilage at a defect site include autologous chondrocyte transplantation (ACT), which implants chondrocytes (alone or in combination with a cartilage matrix) at a defect site, and mosaicplasty, which implants autografts or allografts at a defect site. In ACT, chondrocytes are harvested from a non-weight bearing portion of the joint and expanded in vitro prior to implanting into the defect. In mosaicplasty, osteochondral plugs are harvested from non-weight bearing portions of a joint and inserted into the defect site. Depending on the defect and other considerations, either procedure may be carried out by open surgery or arthroscopically. Although some weight-bearing relief may be achieved for some patients by these procedures, the sites of implantation generally progress to a less organized architecture than healthy hyaline cartilage in combination with a fibrocartilage tissue. Accordingly, such replacement tissue lacks the characteristics and integrity of authentic articular cartilage.

The generally poor results for treating full thickness defects by the procedures described above continue to reinforce the general belief in orthopedic surgery that it is best to not disturb asymptomatic partial thickness defects as current procedures would only remove the remnant of healthy cartilage at a defect site prematurely to introduce an inferior fibrocartilage tissue.

The use of biochemical signaling molecules, such as bone morphogenetic proteins (BMPs), to regenerate cartilage at a defect site has also been studied. For example, cells migrating into a cartilage defect were transformed into chondrocyte-like cells and even produced type I collagen fibers in the presence of a BMP that was exogenously applied to the defect area (Jelic et al., *Growth Factors*, 19(2): 101-113 (2001)). However, such tissue did not display the characteristic columnar microarchitecture of authentic articular cartilage and thus lacked the biomechanical and structural properties that enable authentic articular cartilage to function and persist in the joint.

Clearly, needs remain for joint preserving procedures to treat partial thickness defects in a manner that restores the characteristic structural and biochemical properties of healthy articular cartilage and thereby inhibit or prevent the development of full thickness defects and the onset of osteoarthritis.

SUMMARY OF THE INVENTION

The invention solves the above problems by providing methods and compositions that regenerate cartilage at a site of a partial thickness defect or area of reduced volume of articular cartilage in an individual (human or other vertebrate). The cartilage regenerated according to the invention has the architectural and biochemical properties characteristic of authentic hyaline cartilage of a healthy joint and thus provides restoration of articular cartilage tissue in kind instead of filling a defect with a fibrocartilaginous repair tissue that has an inferior integrity and does not persist.

In one embodiment, the invention provides a method of treating a partial thickness defect or area of reduced volume of articular cartilage in the joint of an individual comprising:

administering to the partial thickness defect or area of reduced volume of articular cartilage an infiltration suppressor agent that suppresses or inhibits infiltration of synoviocytes, fibroblasts (including fibroblast-like cells), and/or subchondral bone marrow cells into the defect or area, and administering to the partial thickness defect or area of reduced volume of articular cartilage a columnar growth promoting agent that promotes columnar growth of chondrocytes in the defect or area.

An infiltration suppressor agent useful in the methods and compositions described herein may be any compound or combination of compounds that inhibits or suppresses the migration and/or growth of synoviocytes, fibroblasts (including fibroblast-like cells), and/or subchondral bone marrow cells into a partial thickness defect or area of reduced volume of articular cartilage in a joint of an individual. Preferred compounds useful as infiltration suppressor agents include, but are not limited to, corticoid steroids, cartilage derived morphogenetic proteins (CDMPs), and combinations thereof. A preferred corticoid steroid is dexamethasone. Preferably, the CDMP is CDMP-1 or CDMP-2. In a particularly preferred embodiment, the infiltration suppressor agent is a combination of dexamethasone and CDMP-2.

A columnar growth promoting agent useful in the methods and combinations described herein may be any compound or combination of compounds that promotes or stimulates growth of chondrocytes in the characteristic columnar architecture found in normal hyaline cartilage and, preferably, also promotes or stimulates the production of cartilage specific components, such as type II collagen, type VI collagen, aggrecan, and proteoglycans, by the chondrocytes in the defect or area of reduced volume of articular cartilage. Preferred compounds useful as columnar growth promoting agents include, but are not limited to, bone morphogenetic proteins (BMPs), fibroblast growth factors (FGFs, such as FGF-8), insulin-like growth factors (IGFs, such as IGF-1), and combinations thereof. More preferably, the columnar growth promoting agent is a BMP such as BMP-2, BMP4, BMP-6, BMP-7, heterodimers thereof, and combinations thereof.

The infiltration suppressor agent and the columnar growth promoting agent may be administered into a defect or area of reduced volume of articular cartilage by injection with a syringe during open surgery or arthroscopically. Preferably, the infiltration suppressor agent and columnar growth promoting agent are injected arthroscopically.

The infiltration suppressor agent and the columnar growth promoting agent may be administered separately or mixed together and the mixture administered to the defect site or area of reduced volume of articular cartilage.

The infiltration suppressor agent and the columnar growth promoting agent may also be formulated with one or more other agents that have a beneficial activity or property. Such formulations may comprise an effective amount of an infiltration suppressor agent or a columnar growth promoting agent in combination with a pharmaceutically acceptable carrier or buffer, and may further include one or more other ingredients such as other medicinal agents (e.g., antibiotics, anti-inflammatory compounds, anti-viral agents, anti-cancer agents, etc.), diluents, fillers, formulation adjuvants, and combinations thereof, which are non-toxic and pharmaceutically acceptable.

DETAILED DESCRIPTION OF THE INVENTION

Figure 1:
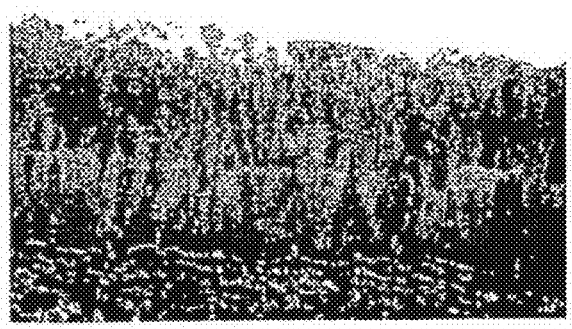
FIG. 1 is a photograph of newly regenerated cartilage in a partial thickness defect in the articular cartilage of a knee of a sheep in the study described in Example 1. The photograph shows the columnar outgrowth of newly formed cartilage with chondrocytes formed in the deep intact layer of the partial chondral defect. The formation of the newly formed cartilage begins in the intact layer with outgrowth of the new cartilage to the surface. The deeper layer of the newly formed cartilage is rich in type II collagen. The superficial (top) layer is not columnar, which is also characteristic of normal articular architecture. A light thin horizontal line marks the interface between original intact cartilage at the base of the partial thickness defect and the newly regenerated cartilage.

The invention is based on the discovery that authentic hyaline cartilage can be regenerated at a partial thickness defect in articular (joint) cartilage, i.e., at a defect in the cartilage that does not penetrate to the subchondral bone, when the normal repair response that typically generates inferior fibrocartilaginous material is sufficiently suppressed or inhibited to permit the slower process of authentic chondrogenesis to proceed. Methods and compositions described herein thus provide the means to regenerate authentic hyaline cartilage at the site of a partial thickness defect in the joint of an individual instead of being filled with an inferior fibrocartilaginous repair tissue, which typically does not persist and cannot prevent the eventual degeneration (increasing in diameter and depth) of the partial thickness defect to become a full thickness defect that penetrates to and exposes the subchondral bone. Accordingly, by regenerating authentic cartilage at the site of a partial thickness defect, the methods and compositions described herein may be used to prevent the development of osteoarthritis. In addition, the methods described herein may be carried out arthroscopically and thereby avoid open surgery and scarring of the soft tissues surrounding the joint space and the patient's skin over the joint (e.g., at the knee or elbow).

Methods of the invention for treating a partial thickness defect or an area of reduced volume of articular cartilage in the joint of an individual comprise:

administering to the partial thickness defect or area of reduced volume of articular cartilage an infiltration suppressor agent that suppresses or inhibits infiltration of synoviocytes, fibroblasts (including fibroblast-like cells), and/or subchondral bone marrow cells into the defect or area, and administering to the partial thickness defect or area of reduced volume of articular cartilage a columnar growth promoting agent that promotes columnar growth of chondrocytes in the defect or area.

An "infiltration suppressor agent" useful in the methods and compositions described herein may be any compound or combination of compounds that suppresses or inhibits migration or growth of various repair cells such as synoviocytes, fibroblasts (including fibroblast-like cells), and bone marrow cells that by migration and/or growth are able to rapidly infiltrate a partial thickness defect or area of reduced volume of articular cartilage. Examples of compounds that are known to inhibit migration or proliferation of such cells and, therefore, may be used as an infiltration suppressor agent, include, but are not limited to, corticoid steroids (e.g., dexamethasone), cartilage derived morphogenetic proteins (CDMPs, e.g., CDMP-1, CDMP-2), and combinations thereof. CDMP-1 is also known in the art as "GDF-5", "BMP-14", or "MP-52". CDMP-2 is also known in the art as "GDF-6" or "BMP-13". A preferred infiltration suppressor agent that is useful in the methods and combinations described herein is a combination or mixture of dexamethasone and CDMP-2. Dexamethasone and CDMP-2 may be administered individually by local injection into a defect or area of reduced volume of articular cartilage, or the two drugs may be combined and injected together into the defect or area.

Standard assays using cell cultures permit a compound or combination of compounds to be tested for the ability to inhibit growth of synoviocytes, fibroblasts, or bone marrow cells and, therefore, to be used as an infiltration suppressor agent (see, e.g., Lories et al., *Ann. Rheum. Dis.*, 62(6): 568-571 (2003)). Compounds that inhibit migration may be identified by the ability to inhibit synthesis of molecules that stimulate migration by such migratory cells in culture, e.g., in cultures of primary synoviocytes (see, e.g., Vandenabeele et al., *Arch. Histol. Cytol.*, 66(2): 145-153 (2003)). Such assays may detect the synthesis (or inhibition of synthesis) of a migration-related peptide or polypeptide or of the mRNA transcripts encoding one or more migration-related peptides or polypeptides using any of a variety of standard detection systems, e.g., antibody-based detection systems, Northern blots, polymerase chain reaction (PCR) methods, and the like.

When the migration or growth of synoviocytes, fibroblasts, and/or subchondral bone cells into a defect site is suppressed or inhibited, local chondrocytes are provided sufficient time and space to migrate out of their lacunae through the cartilage matrix and into the defect site where they can begin to proliferate and produce components of the hyaline cartilage, i.e., initiate chondrogenesis.

A "columnar growth promoting agent" is any compound or combination of compounds that promotes or stimulates growth of chondrocytes in a columnar architecture characteristic of normal hyaline cartilage (see, e.g., FIGS. 1-3) and, preferably, also promotes or stimulates the production of cartilage specific components, such as type II collagen, type VI collagen, aggrecan, and proteoglycans, by the chondrocytes.

Examples of compounds that promote or stimulate chondrocyte growth and the production of cartilage components are known in the art. Such compounds include the bone morphogenetic proteins (BMPs). A "bone morphogenetic protein" ("BMP", "morphogen") refers to any member of a particular subclass (i.e., the BMP family) of the transforming growth factor-$\beta$ (TGF-$\beta$) super family of proteins (see, e.g., Hoffmann et al., *Appl. Microbiol. Biotechnol.*, 57: 294-308 (2001); Reddi, *J. Bone Joint Surg.*, 83-A(Supp. 1): S1-S6 (2001); U.S. Pat. Nos. 4,968,590; 5,011,691; 5,674,844; 6,333,312). BMPs are preferred for use as a columnar growth promoting agent in the methods and compositions described herein.

All such BMPs have a signal peptide, prodomain, and a carboxy-terminal (mature) domain. The carboxy-terminal domain is the mature form of the BMP monomer and contains a highly conserved region characterized by seven cysteines that form a cysteine knot (see, Griffith et al., *Proc. Natl. Acad. Sci. USA*, 93: 878-883 (1996)). BMPs were originally isolated from mammalian bone using protein purification methods (see, e.g., Urist et al., *Proc. Soc. Exp. Biol. Med*, 173: 194-199 (1983); Urist et al., *Proc. Natl. Acad. Sci. USA*, 81: 371-375 (1984); Sampath et al., *Proc. Natl. Acad. Sci. USA*, 84: 7109-7113 (1987); U.S. Pat. No. 5,496,552). However, BMPs have also been detected in or isolated from other mammalian tissues and organs including kidney, liver, lung, brain, muscle, teeth, and gut. BMPs may also be produced using standard in vitro recombinant DNA technology for expression in prokaryotic or eukaryotic cell cultures (see, e.g., Wang et al., *Proc. Natl. Acad. Sci. USA*, 87: 2220-2224 (1990); Wozney et al., *Science*, 242: 1528-1534 (1988)). Some BMPs are commercially available for local use as well (e.g., BMP-7 is manufactured and distributed for treatment of long bone non-union fractures by Stryker-Biotech (Hopkinton, Mass.); BMP-2 is manufactured and distributed for long bone acute fractures by Wyeth (Madison, N.J.), and also for spinal fusions (Medtronic, Inc., Minneapolis, Minn.)).

BMPs normally exist as dimers of the same monomeric polypeptides (homodimers) held together by hydrophobic interactions and at least one interchain (between monomers) disulfide bond. However, BMPs may also form heterodimers by combining the monomers of different degrees (lengths) of processing (e.g., a full-length, unprocessed monomer associated with a processed, mature monomer) or monomers from different BMPs (e.g., a BMP-6 monomer associated with a BMP-7 monomer). A BMP dimer of unprocessed monomers or a BMP heterodimer of one processed BMP monomer and one unprocessed BMP monomer are typically soluble in aqueous solutions, whereas a BMP homodimer comprised of two fully processed (mature) monomers is only soluble in an aqueous solution at a low pH (e.g., acetate buffer, pH 4.5) (see, e.g., Jones et al., *Growth Factors*, 11: 215-225 (1994)).

Although not employed in this invention to promote bone formation, BMPs useful in the compositions and methods described herein are those that have osteoinductive activity, i.e., the ability to stimulate bone formation. When administered locally to a joint to treat a partial thickness defect or to an area of reduced volume of articular cartilage, such osteoinductive BMPs promote the columnar growth of chondrocytes and the synthesis of cartilage components by such cells. Without intending to be bound by any particular mechanism, it is noted that osteoinductive BMPs promote bone formation by a process wherein cartilage is first formed by chondrocytes and eventually replaced with bone by osteoblasts and osteocytes. Due to the lack of angiogenesis, articular cartilage and the joint environment do not provide the proper substrate for the entire process of bone formation to occur.

Osteoinductive (or "osteogenic") activity may be detected using any of a variety of standard assays. Such osteoinductive assays include ectopic bone formation assays in which a carrier matrix comprising collagen and a BMP are implanted at an ectopic site in a rodent, and the implant then monitored for bone formation (Sampath and Reddi, *Proc. Natl. Acad. Sci. USA*, 78: 7599-7603 (1981)). In a variation of such an assay, the matrix may be implanted at an ectopic site and the BMP administered to the site, e.g., by intravenous injection into the rodent. Another way to assay for BMP osteoinductive activity is to incubate cultured fibroblast progenitor cells with a BMP and then monitor the cells for differentiation into chondrocytes and/or osteoblasts (see, e.g., Asahina et al., *Exp. Cell. Res.*, 222: 38-47 (1996)).

BMPs that have osteoinductive activity and therefore are useful in the invention as columnar growth promoting agents of chondrocytes include, but are not limited to, BMP-2 (BMP-2A), BMP-4 (BMP-2B), BMP-6, BMP-7, BMP-9, heterodimers thereof, and combinations thereof, whether purified from a natural source, produced recombinantly by eukaryotic (e.g., mammalian) or prokaryotic (e.g., *Escherichia coli*) cells, or produced in whole or in part by in vitro protein synthesis methods.

As noted above CDMP-1 is identical to BMP-14, and CDMP-2 is identical to BMP-13. Both of these BMPs are osteoinductive. Accordingly, CDMP-1 or CDMP-2 may be used as an infiltration suppressor agent and as a columnar growth promoting agent for chondrocytes in the methods and compositions described herein. However, more preferably, methods and compositions of the invention use a CDMP in combination with a corticoid steroid (e.g., dexamethasone) as the infiltration suppressor agent and use another BMP (e.g., BMP-2, BMP4, BMP-6, BMP-7) as the columnar growth promoting agent.

Assays are also available for testing whether a compound has the property to stimulate chondrocyte proliferation and/or the synthesis of cartilage specific components by chondrocytes (see, e.g., Luyten et al., *J. Biol. Chem.*, 267(6): 3691-3695 (1992)). Accordingly, such assays may be employed to determine whether a compound or combination of compounds may be useful in the invention as a columnar growth promoting agent. Thus, it is understood that compositions and methods comprising an osteoinductive BMP as a columnar growth promoting agent may alternatively comprise a protein other than a known osteoinductive BMP provided such protein promotes columnar growth of chondrocytes at a partial thickness defect or area of reduced volume of articular cartilage. Examples of compounds that are not BMPs and that may be used as columnar growth promoting agents in the invention include, but are not limited to, chondrogenic fibroblast growth factors (FGFs, such as FGF-8), and insulin-like growth factors (IGFs, such as IGF-1).

By "pharmaceutically acceptable" is meant a material that is not biologically, chemically, or in any other way incompatible with body chemistry and metabolism and also does not adversely affect the desired, effective activity of one or more components used in the methods and compositions described herein to regenerate articular cartilage.

A composition or method described herein as "comprising" one or more named elements or steps is open-ended meaning that the named elements or steps are essential, but other elements or steps may be added within the scope of the composition or method. To avoid prolixity, it is also understood that any composition or method described as "comprising" (or "comprises") one or more named elements or steps also describes the corresponding, more limited, composition or method "consisting essentially of" (or "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and close-ended composition or method "consisting of" (or "consists of") the named elements or steps to the exclusion of any other unnamed element or step. In any composition or method disclosed herein, known or disclosed equivalents of any named essential element or step may be substituted for that element or step.

In addition to examining articular cartilage during open surgery, partial thickness defects and areas of reduced volume of articular cartilage are readily detected by arthroscopic examination. In addition, corticoid steroids, CDMPs, BMPs, FGFs, IGFs, and many other compounds may be formulated for injection into a partial thickness defect with the aid of an arthroscope. Subsequent examination for the progress in cartilage regeneration may also be carried out arthroscopically.

In some cases, it may be necessary to trim or sculpture a defect or area in the articular cartilage to remove tissue debris and/or to provide a well-defined site for administering the infiltration suppressor agent and columnar growth promoting agent. In sculpting a partial thickness defect for treatment according to the invention, care should be taken to retain at least one, preferably more than one, and more preferably three or more layers of chondrocytes at the base of the cartilage defect or area to be treated as this layer serves as the primary source of chondrocytes that will migrate and grow into the defect site and also serves as a barrier to the possible migration and ingrowth of subchondral bone marrow cells. Such trimming and sculpturing of an area of articular cartilage is readily performed arthroscopically by the healthcare professional.

A partial thickness defect or area of reduced volume of articular cartilage in an individual is treated by administering an infiltration suppressor agent and a columnar growth promoting agent into the affected joint. Preferably, these agents are injected with a syringe as closely as possible into the defect or area of interest, although typically the agents that are injected into the joint are likely to bathe the entire surface of the affected cartilage. Care is taken by the healthcare professional in administering the agents so as not to penetrate or disturb the cartilage surface with the needle on the syringe, not to scratch any bone surface, and not to inject the agents into muscle tissue or a blood vessel as these soft tissues may yield some degree of ectopic bone formation.

Any of a variety of pharmaceutically acceptable carriers (vehicles, buffers) may be used to formulate an infiltration suppressor agent and a columnar growth promoting agent for use in the methods and compositions described herein. Preferably, the agents are formulated for local administration by injection as a liquid formulation at the site of a partial thickness defect or area of reduced volume of articular cartilage. Such formulations may comprise an effective amount of an infiltration suppressor agent or a columnar growth promoting agent in combination with a pharmaceutically acceptable carrier or buffer, and may further include one or more other ingredients such as other medicinal agents (e.g., antibiotics, anti-inflammatory compounds, anti-viral agents, anti-cancer agents, etc.), carriers, diluents, fillers, formulation adjuvants, and combinations thereof, which are non-toxic and pharmaceutically acceptable. In liquid formulations for injection into a defect site, a pharmaceutically acceptable carrier may be a buffer solution, such as a phosphate buffered saline or a pharmaceutically acceptable, especially isotonic, aqueous buffer. The pH may be adjusted in such formulations as necessary, e.g., to promote or maintain solubility of one or more compounds, to maintain stability of one or more ingredients in the formulation, and/or to deter undesired growth of microorganisms that potentially may be introduced at some point in the procedure.

In osteoarthritis, the articular cartilage that normally protects the articular ends of the bones in a joint is lost or worn away. The loss of adequate articular cartilage is usually the result of the progressive degeneration of a partial thickness defect into a full thickness defect that penetrates to the subchondral bone. Eventually, so much articular cartilage is lost or worn away that no cartilage layer protects one or both articular surfaces of the opposing bone ends from contacting, impacting, and grinding one another. Symptoms of osteoarthritis include joint pain, internal bleeding in the joint bones, and decreased mobility. No satisfactory treatment is currently available to restore the lost articular cartilage. Accordingly, treatment for patients of osteoarthritis is primarily palliative (e.g., pain medication, limiting mobility) or surgical, such as knee replacement with a prosthetic joint. The methods and compositions described herein to regenerate authentic cartilage at partial thickness defects thus provide a new approach for the prevention of osteoarthritis in an individual.

The methods and compositions described herein may also be used to treat any articular cartilage that is characterized by a decreased volume of cartilage. In addition to the development of partial thickness defects, the overall volume of cartilage in a joint may be diminished by trauma or various diseases. The methods and compositions described herein may be applied to areas of such cartilage wherever one or more layers of chondrocytes remain to regenerate and increase the total volume of articular cartilage in the joint. Even if the entire articular area is so damaged that it cannot be restored to its original volume of healthy cartilage, the methods and compositions described herein may provide areas of regenerated cartilage that are sufficient to protect the joint from osteoarthritis. Moreover, treatment of such severely affected joints with the methods and compositions described herein may be repeated as necessary to maintain the articular cartilage in an individual and thereby prevent the development of osteoarthritis and the need for joint replacement surgery.

Additional embodiments and features of the invention will be apparent from the following non-limiting examples.

EXAMPLES

Example 1

Regeneration of Articular Cartilage by Full Restoration of its Normal Structure In Vivo Owing to the specific architecture in cartilage, chondrocytes need more time to initiate the regeneration process than osteoblasts require to regenerate bone. For this reason, the migration or growth into the site of a partial thickness defect of articular cartilage by competing migratory and faster growing cells such as synoviocytes, fibroblasts from the synovial fluid, and subchondral bone marrow cells, must be suppressed or inhibited by administering an infiltration suppressor agent into the area of the defect. A columnar growth promoting agent is also administered to promote growth of chondrocytes and synthesis of cartilage components by those chondrocytes. Cocktail A: 10 micromol (μmol) of dexamethasone and 40 micrograms (μg) of CDMP-2 (cartilage-derived morphogenetic protein-2) both slightly inhibiting migration and inhibiting proliferation of synoviocytes and synovial joint fluid fibroblasts, while use in parallel also stimulates proliferation and differentiation of chondrocytes residing at the bottom of surgically created defects. The first injection was applied to sheep knee joint on the third day following surgery. At 10 days following surgery, a second injection was administered containing dexamethasone and CDMP-2, as described above, and also BMP-7 (50 μg) to further promote the phenotype of chondrocytes migrating out of the remnant defect chondrocytic lacunae and forming appropriately shaped columns with perpendicularly deposited extracellular matrix. The content of the second injection was administered three more times: at day 40, 70, and 120 following surgery. The animals were sacrificed 8 months following surgery.

Cocktail B: 10 μmol of dexamethasone and 40 μg of CDMP-2 were administered as a first injection to joints of sheep at three days following the surgery. At 10 days following surgery, a second injection containing dexamethasone and CDMP-2, as described above, and also 50 μg of BMP-4. The content of the second injection was administered three more times: at day 40, 70, and 120 following surgery.

Cocktail C: tested only in vitro on mixed articular cartilage explants and synoviocyte cultures. The cocktail contained 40 μg of CDMP-2 in the first injection on day three (from starting the culture). The second injection, given at day 10 following the first injection, contained 20 μg of FGF-8 and 50 μg of BMP-7 (OP-1). Cocktail C was used to define an in vitro model for testing various compositions of proteins and related molecules, as described herein, for use in designing new therapies for articular chondrocyte regrowth.

In seventeen sheep, chondral defects were surgically created that retained at least a layer of chondrocytes at the base of the defects (50 μm). This provided a remnant of articular chondrocytes of about three lacunar layers (by using precisely designed instruments for microscopic removal of cell layers). Animals were divided into the following treatment groups:

1. control (untreated) sheep (n=5)
2. sheep injected with cocktail A as described above (n=6)
3. sheep injected with cocktail B as described above (n=6).

Results
Cocktails A and B

Animals were treated for eight months and five injections of a cocktail in a weekly manner as described above. Animals were sacrificed following arthroscopy. In animals treated with Cocktail A or B, chondral defects were fully or partially regenerated by formation of new articular chondrocytes organized into columns with perpendicularly oriented (i.e., relative to the horizontal base of the defect) chondrocytic lacunae as well as newly deposited extracellular matrix (see, FIGS. 1-3). Control sheep that were not treated with Cocktail A or B had empty chondral defects with occasional perforation of the subchondral layer and underlying bone cysts.

Figure 2:
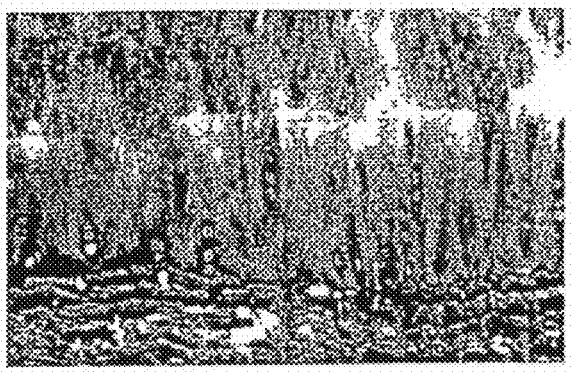
FIG. 2 provides a higher magnification of the tissue in FIG. 1 showing the interface between intact cartilage and newly formed cartilage. Some columns as well as some lacunae are seen residing in both the intact and newly formed cartilage indicating that the origin of the newly formed cartilage is the intact layer.
Figure 3:
FIG. 3 shows columnar outgrowth of newly regenerated articular cartilage in the knee of a sheep in Example 1 with a special view of the collagen fibers that are oriented in the deep layer of the newly formed cartilage in a manner perpendicular to the base of the partial thickness defect. This is a feature of normal microarchitecture of healthy articular cartilage.

As shown in FIGS. 1-3, the cartilage in defects treated with a cocktail according to the invention had a columnar structure, with chondrocytes protruding out from the underlying thin layer. Proliferation of chondrocytes in the remnant layer (base of the defect) and newly formed cells above was intense. The collagen and proteoglycan accumulation followed the columnar pattern of newly formed chondrocyte lacunae (FIG. 3). In the newly formed superficial zone, a typical superficial cartilage layer was found with intensively proliferating cells. Newly formed cells did not synthesize type X collagen, which is a marker for osteogenesis, thus confirming that the new cartilage was a permanent tissue not undergoing osteogenesis.

These results show for the first time that articular chondrocytes retain a capacity to regenerate if not invaded by other cells from the joint compartment which proliferate and move much faster than the matrix-embedded chondrocytes, which need more time to find a way out of the matrix and to protrude into the chondral defect area where they can proliferate and slowly deposit new cartilage matrix of columnar structure (FIG. 1). Also important is the fact that the newly formed cartilage was well incorporated with the matrix comprising the walls of the defects indicating that the newly formed tissue will be mechanically competent during weight bearing.

The use of the cocktail enabled the regeneration process to take place, but the process takes a relatively long time to obtain columns, which even after 8 months were not fully hyaline cartilage, similar to the residing matrix from the bottom of the chondral defect. Treatment of a partial thickness defect in articular cartilage by administering an infiltration suppressor agent and a columnar growth promoting agent thus provides the time, space, and activities necessary for endogenous chondrocytes of the surrounding cartilage matrix to eventually regenerate articular cartilage at the site of a partial thickness defect.

Cocktail C

Histological and biochemical analyses revealed that the use of Cocktail C stimulated proliferation of and matrix synthesis by chondrocytes in cartilage explant cultures while at the same time inhibiting proliferation of and matrix synthesis by synoviocytes. Specifically, Cocktail C stimulated synthesis of proteoglycans and type II collagen by chondrocytes and inhibited type I collagen synthesis by synoviocytes. Importantly, the amount of agents in Cocktail C did not transform synoviocytes into chondrocytes.

All patents, applications, and publications cited in the above text are incorporated herein by reference.

Other variations and embodiments of the invention described herein will now be apparent to those of skill in the art without departing from the disclosure of the invention or the claims below.

The invention claimed is:

1. A method of treating a partial thickness defect or area of reduced volume of articular cartilage in the joint of an individual comprising the steps:
   a. administering to the partial thickness defect or area of reduced volume of articular cartilage an effective amount of an infiltration suppressor agent that suppresses or inhibits infiltration of synoviocytes, fibroblasts, or subchondral bone marrow cells into the defect or area, wherein the infiltration suppressor agent is a corticoid steroid or a combination of a corticoid steroid and a cartilage derived morphogenetic protein (CDMP), and
   b. administering to the partial thickness defect or area of reduced volume of articular cartilage an effective amount of a columnar growth promoting agent that promotes columnar growth of articular chondrocytes in the defect or area, wherein the columnar growth promoting agent is selected from the group consisting of a bone morphogenetic protein (BMP), an insulin-like growth factor (IGF), a fibroblast growth factor (FGF), and combinations thereof.

2. The method according to claim 1, wherein the corticoid steroid is dexamethasone.

3. The method according to claim 1, wherein the CDMP is CDMP-1 or CDMP-2.

4. The method according to claim 1, wherein the infiltration suppressor agent is a combination of dexamethasone and CDMP-2.

5. The method according to claim 1, wherein the BMP is selected from the group consisting of BMP-2, BMP-4, BMP-6, BMP-7, BMP-9, heterodimers thereof, and combinations thereof.

6. The method according to claim 1, wherein the FGF is FGF-8.

7. The method according to claim 1, wherein the IGF is IGF-1.

8. The method according to claim 1, wherein the columnar growth promoting agent is a combination of a BMP and an FGF.

9. The method according to claim 8, wherein the FGF is FGF-8.

10. The method according to claim 1, wherein the infiltration suppressor agent and the columnar growth promoting agent are administered to the defect site or area of reduced volume of articular cartilage separately.

11. The method according to claim 1, wherein steps a. and b. are performed simultaneously.

12. The method according to claim 1, wherein the infiltration suppressor agent is administered to the defect site or area of reduced volume of articular cartilage and thereafter the infiltration suppressor agent is mixed with the columnar growth promoting agent and that mixture is then administered to the defect site or area of reduced volume of cartilage.

13. The method according to claim 1, wherein the defect is surgically modified to provide a well defined defect site or area of reduced volume of articular cartilage prior to administering the infiltration suppressor agent or the columnar growth promoting agent.

14. A method of treating a partial thickness defect or area of reduced volume of articular cartilage in the joint of an individual comprising the steps:
   a. administering to the partial thickness defect or area of reduced volume of articular cartilage an effective amount of an infiltration suppressor agent that suppresses or inhibits infiltration of synoviocytes, fibroblasts, or subchondral bone marrow cells into the defect or area, wherein the infiltration suppressor agent is a corticoid steroid or a combination of a corticoid steroid and a cartilage derived morphogenetic protein (CDMP), and
   b. administering to the partial thickness defect or area of reduced volume of articular cartilage an effective amount of a columnar growth promoting agent that promotes columnar growth of articular chondrocytes in the defect or area, wherein the columnar growth promoting agent is a bone morphogenetic protein (BMP) selected from the group consisting of BMP-2, BMP-4, BMP-6, BMP-7, BMP-9, heterodimers thereof, and combinations thereof.

15. The method according to claim 14, wherein the corticoid steroid is dexamethasone.

16. The method according to claim 14, wherein the CDMP is CDMP-1 or CDMP-2.

17. The method according to claim 14, wherein the infiltration suppressor agent is a combination of dexamethasone and CDMP-2.

* * * * *